United States Patent
Julia et al.

(10) Patent No.: US 11,033,922 B2
(45) Date of Patent: Jun. 15, 2021

(54) DEVICE FOR DISTRIBUTING LIQUID IN THE FORM OF DROPS

(71) Applicants: Xavier Julia, Villefontaine (FR); Gaetan Painchaud, Francheville (FR); Guillaume Grevin, L'Isle d'Abeau (FR)

(72) Inventors: Xavier Julia, Villefontaine (FR); Gaetan Painchaud, Francheville (FR); Guillaume Grevin, L'Isle d'Abeau (FR)

(73) Assignee: Nemera La Verpillière

( * ) Notice: Subject to any disclaimer, the term of this patent is extended or adjusted under 35 U.S.C. 154(b) by 0 days.

(21) Appl. No.: 14/346,231

(22) PCT Filed: Sep. 24, 2012

(86) PCT No.: PCT/FR2012/052127
§ 371 (c)(1),
(2) Date: Mar. 20, 2014

(87) PCT Pub. No.: WO2013/041819
PCT Pub. Date: Mar. 28, 2013

(65) Prior Publication Data
US 2014/0231536 A1    Aug. 21, 2014

(30) Foreign Application Priority Data
Sep. 22, 2011 (FR) ...................... 1158469

(51) Int. Cl.
*B05B 13/00* (2006.01)
*A61F 9/00* (2006.01)
*B65D 47/18* (2006.01)

(52) U.S. Cl.
CPC ............ *B05B 13/00* (2013.01); *A61F 9/0008* (2013.01); *B65D 47/18* (2013.01); *A61F 2250/005* (2013.01)

(58) Field of Classification Search
CPC ...... B05B 13/00; A61F 9/0026; A61F 9/0008; A61F 2250/005; A61M 35/003;
(Continued)

(56) References Cited

U.S. PATENT DOCUMENTS

| 4,550,866 A | 11/1985 | Moore |
| 4,629,456 A | 12/1986 | Edwards |

(Continued)

FOREIGN PATENT DOCUMENTS

| DE | 8910409 U1 | 2/1990 |
| DE | 102009048476 B3 | 9/2010 |

(Continued)

OTHER PUBLICATIONS

Office Action from China with Partial Translation Application No. 201280045868.2 dated Dec. 29, 2014 7 pages.

(Continued)

*Primary Examiner* — Joseph A Greenlund
*Assistant Examiner* — Steven M Cernoch
(74) *Attorney, Agent, or Firm* — St. Onge Steward Johnston & Reens, LLC

(57) ABSTRACT

The device includes a drop dispenser orifice formed in a dispenser end, and a mechanism for visually locating the orifice, by forming a demarcation zone having a color that contrasts strongly with other portions of the dispenser end.

9 Claims, 2 Drawing Sheets

(58) Field of Classification Search
CPC . A61M 11/008; A61M 2205/59; B65D 47/18; B65D 1/08; B65D 1/32; B65D 47/205; B65D 47/2081; B65D 90/48; B01L 3/0272
USPC ............... 239/71, 73; 604/300; 222/41, 422
See application file for complete search history.

(56) References Cited

U.S. PATENT DOCUMENTS

| | | | | |
|---|---|---|---|---|
| 4,739,906 | A * | 4/1988 | LoTurco | A61J 1/1443 222/212 |
| 5,310,094 | A * | 5/1994 | Martinez | B05B 11/0075 222/212 |
| 5,373,964 | A * | 12/1994 | Moore | 222/1 |
| 5,558,653 | A * | 9/1996 | Lindstrom | 604/300 |
| 5,584,823 | A * | 12/1996 | Valberg | 604/294 |
| 5,678,729 | A * | 10/1997 | Raymond | 222/23 |
| 5,932,206 | A * | 8/1999 | Pine | A61F 9/0008 424/78.04 |
| 5,976,116 | A * | 11/1999 | Muroff | 604/294 |
| 6,223,947 | B1 * | 5/2001 | Bernard | A61F 9/0008 222/113 |
| 7,249,694 | B2 * | 7/2007 | Masuda | 222/212 |
| 7,303,098 | B2 * | 12/2007 | Backes | B65D 47/2018 222/212 |
| 7,306,129 | B2 * | 12/2007 | Swiss | B65D 47/205 137/853 |
| 7,699,193 | B2 * | 4/2010 | Feierabend | F16K 21/04 222/490 |
| 8,616,418 | B2 * | 12/2013 | Painchaud | B65D 47/18 222/422 |
| 8,690,019 | B2 * | 4/2014 | Defemme | B65D 47/18 137/513.5 |
| 8,820,578 | B2 * | 9/2014 | Kneer | B65D 47/2081 222/105 |
| 8,863,998 | B2 * | 10/2014 | Painchaud | B65D 47/2031 222/494 |
| 8,955,715 | B2 * | 2/2015 | Kneer | B65D 83/0055 222/105 |
| 2002/0016576 | A1 | 2/2002 | Lee | |
| 2008/0039807 | A1 * | 2/2008 | Pine | 604/295 |
| 2010/0116852 | A1 * | 5/2010 | Painchaud | B05B 11/00444 222/422 |
| 2011/0079300 | A1 | 4/2011 | Kneer | |
| 2011/0155770 | A1 | 6/2011 | Painchaud et al. | |

FOREIGN PATENT DOCUMENTS

| | | |
|---|---|---|
| JP | S60160836 U | 10/1985 |
| JP | 2003033422 A | 2/2003 |
| JP | 3152970 U | 7/2009 |
| WO | 2004013009 A1 | 2/2004 |
| WO | 2008068911 A1 | 6/2008 |
| WO | 2011030062 A1 | 3/2011 |
| WO | 2011051602 A1 | 5/2011 |

OTHER PUBLICATIONS

International Search Report & Written Opinion of the International Searching Authority Application No. PCT/FR2012/052127 Completed: Jan. 14, 2013; dated Jan. 21, 2013 3 pages.

Decision of Rejection Japanese Application No. 2014-531296 dated Jul. 5, 2016 7 pages.

* cited by examiner

DEVICE FOR DISTRIBUTING LIQUID IN THE FORM OF DROPS

FIELD OF THE INVENTION

The present invention relates to dispensing liquid, more particularly dispensing it in the form of drops, in the pharmaceutical field, e.g. liquid for the eyes, the nose, the mouth, or the ears. The term "liquid" is used to designate a preparation that is non-solid and non-gaseous and that is viscous to a greater or lesser extent.

BACKGROUND OF THE INVENTION

Dispenser devices are already known that include a dispenser orifice from which drops are dispensed, e.g. a dispenser orifice formed at the center and at the end of a dispenser nozzle that is generally white in color.

It has been found that dispensing drops requires a certain amount of accuracy on the part of the user, very particularly when dispensing a liquid in the eye. Thus, a clumsy movement by the user can easily lead to depositing the drop beside the target zone.

SUMMARY OF THE INVENTION

The present invention seeks to propose a dispenser device that enables the user to dispense drops with greater accuracy.

To this end, the invention provides a dispenser device for dispensing liquid in the form of drops, the device including a drop dispenser orifice formed in a dispenser end, wherein the device includes locator means for visually locating the orifice, by forming a demarcation zone having a color that contrasts strongly with other portions of the dispenser end.

By means of the demarcation zone, the user very easily detects the location of the dispenser orifice, thereby enabling the user to better target delivery of the drop. The demarcation zone is found to be particularly advantageous for dispensing liquid in the eye (eye drop liquid) due to the fact that when the drop is delivered, the device is extremely close to the eye, which consequently cannot focus or accommodate, and which sees the device in very blurred manner, without clearly distinguishing the portions in relief of the device, and thus the location from which the drop is to be dispensed. Furthermore, when dispensing several drops in the eye consecutively, the user's vision is even more blurred after the first drop has been received.

Thus, instead of making a device in which all of the portions have a similar color, generally white, without any contrast between them, the inventors have the idea of forming a strong visual contrast, so as to help the user to locate the orifice, even when the user's vision is blurred. Tests on users have demonstrated that dispensing accuracy is clearly improved.

It should be observed that the term "dispenser orifice" is used to designate the portion of the end from which the drops are dispensed, preferably a conically shaped portion that enables drops to be formed and that is arranged at the center and in the top portion of the dispenser end. In addition, it should be understood that the demarcation zone having a color contrasting strongly with other portions of the dispenser end may, for example, mean that the demarcation zone is very dark while the remainder of the dispenser end is very pale at least in part, or the demarcation zone is very pale while the remainder of the dispenser end is very dark at least in part.

The invention may further include one or more of the following characteristics, taken alone or in combination:

The demarcation zone is formed inside the dispenser orifice. In particular, the demarcation zone is a dark zone that is arranged inside a drop-forming cavity, while the immediate surroundings outside the drop-forming cavity are made in a pale color.

The demarcation zone is arranged around the dispenser orifice. In particular, the demarcation zone is a pale zone that is arranged at or inside the dispenser orifice, preferably as defined by a conical drop-forming cavity, while the immediate surroundings of the dispenser orifice is made in a dark color. For example, the demarcation zone is made in the form of a continuous or discontinuous colored ring that is arranged around the dispenser orifice. The colored ring may be discontinuous, in the form of a discontinuous circular line, e.g. by a circular run of squares, triangles, circles, or any other pattern.

The device includes drop-forming means and the demarcation zone is obtained by coloring the drop-forming means, preferably with a dark color. The drop-forming means are preferably made up of a conical flared shape. In an advantageous embodiment, the drop-forming means are formed in a piece of elastomer material that forms a liquid flow valve. Alternatively, the demarcation zone is arranged around the drop-forming means, e.g. by dark coloring for some or all of a cap surrounding the drop-forming means.

The device includes a dispenser endpiece that is generally substantially cylindrical in shape, the dispenser end having the general shape of a disk, with the dispenser orifice located in its center. When the end of the device is in the form of a surface that is substantially plane and relatively large compared to the surface of the dispenser orifice, unlike a projecting conical nozzle, this embodiment is particularly advantageous due to the fact that it is more difficult for the user to distinguish the dispenser orifice formed at the center of the surface, very particularly if the drops are dispensed in the vicinity of the eye. Furthermore, such a substantially-cylindrical endpiece may be relatively short in the longitudinal direction of the device, so much so that the device is closer to the eye of the user, making it more difficult to focus on and to see the endpiece in three dimensions (as a result of the endpiece presenting fewer shadows), and thus to see the endpiece in clear manner. The use of locator means may thus create a feeling of security for the user.

The disc is of opaque color. In other words, it has a non-transparent color, for example white or of some other color, or with patterns. In this case, the above-proposed device is particularly advantageous, since when the top of the device is opaque and it presents an extensive disc on its end close to the eye, it constitutes an additional impediment for the user since focusing is more difficult than it would be if the disc were transparent.

The endpiece comprises a drop dispenser valve, a valve support fitted on a reservoir, and a cap for pressing the valve against the support, the cap preferably carrying the demarcation zone. For example, the cap has a general shape of a disk that is perforated at its center and that is provided with an annular skirt that comes to pinch the valve against the support. However, the dispensing device can take many other shapes. In particular, the device may be a device without any valve, configured for dispensing liquid in drops, especially for dispensing eye drops. It may also be in form of a pump or a valve.

The demarcation zone is formed by silk-screen printing, pad printing, hot marking, printing by ink jet, or laser marking.

The device is configured for dispensing liquid in an eye.

The invention also provides the use of a device as described above for dispensing liquid in an eye.

The invention also provides a method of manufacturing a device as described above, said method including a marking step in order to form the demarcation zone, e.g. a step of silk-screen printing, pad printing, hot marking, printing by ink jet, or laser marking.

BRIEF DESCRIPTION OF THE DRAWINGS

The invention can be better understood on reading the following description given merely by way of example, and with reference to the drawings, in which.

DETAILED DESCRIPTION OF THE INVENTION

Figure 1:
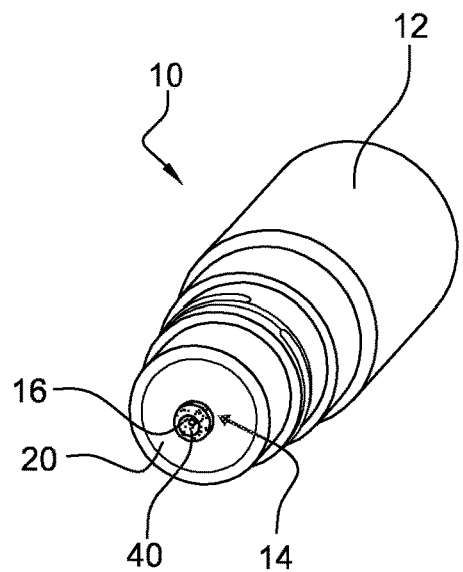
FIG. 1 is a perspective view of a device in an embodiment.
Figure 3:
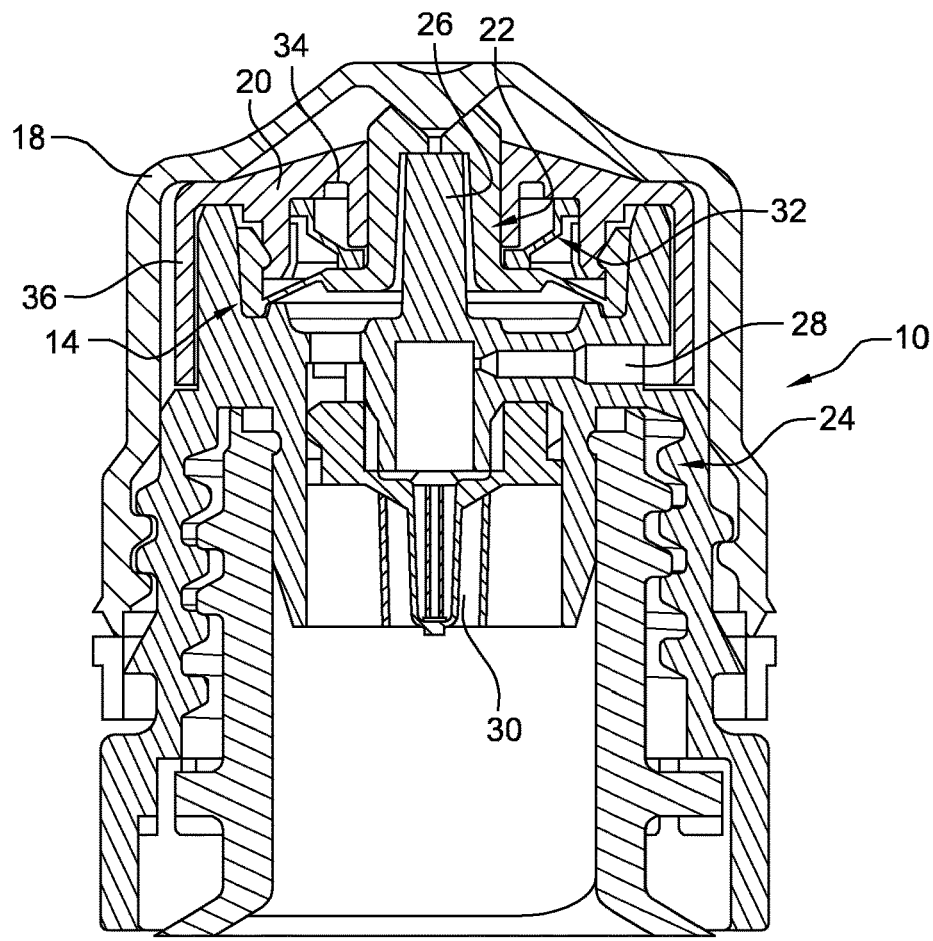
FIG. 3 is a longitudinal section view of the FIG. 1 device, provided with a protective cap.

FIG. 1 shows a dispenser device 10 for dispensing liquid in the form of drops, said device comprising a reservoir 12 on which there is fitted a dispenser endpiece 14 that may be surmounted by a protective cap 18, as can be seen in FIG. 3.

The endpiece 14 presents a top dispenser end 20 in which there is formed a drop dispenser orifice 16 that is defined by drop-forming means 16, in this embodiment. More precisely, still in this embodiment, the endpiece 14 is generally substantially cylindrical in shape, the dispenser end 20 having the general shape of a disk with the dispenser orifice 16 located in its center. This dispenser end 20 having the general shape of a disk is of non-transparent color, for example it is white or of some other solid color, such that it constitutes an impediment for the user bringing it very close to an eye. As can be seen in FIG. 3, the endpiece 14 includes a drop dispenser valve 22 that is made of elastomer material so that, under the pressure of the liquid (when the user presses on the reservoir 12), it takes on a configuration for passing the liquid. The drop-forming means 16 are formed at the end of the valve 22, directly out of the elastomer material. The means 16 are of conical flared shape. The endpiece 14 also includes a valve support 24 that is fitted on the reservoir 12, which support carries a pin 26 that forms a seat against which the valve 22 bears, and also includes an air duct 28 that is closed by a member 30 that is permeable to air, preventing bacteria from being introduced into the reservoir. The endpiece 14 also includes a return element 32 that makes it possible to return the valve 22 into its liquid-blocking configuration. Finally, the endpiece 14 includes a cap 34 for pressing the valve against the support 24, the cap comprising the end 20 in the shape of a substantially-flat disk that is perforated at its center, the disk being provided with an outer annular skirt 36 that is fastened on the support 24 and with an inner guide skirt for guiding the valve 22.

As can be seen in FIG. 1, the device includes locator means 40 for visually locating the orifice, in this embodiment coinciding with the drop-forming means 16, by forming a demarcation zone 40 having a color that contrasts strongly with other portions of the dispenser end. In this embodiment, the demarcation zone 40 is formed inside the dispenser orifice 16 by coloring the drop-forming means. The coloring contrasts strongly with the remainder of the endpiece. In a non-limiting embodiment, the apparent color of the drop-forming means is dark, possibly blue, while the remainder of the endpiece is of a pale color, white.

It should be observed that the dispenser orifice 16 is made substantially in the same plane as the surface 20, so much so that it may be difficult to distinguish it relative to the remainder of the surface 20 when the device 10 is brought close to the eye. It is thus particularly useful to provide a demarcation zone 40. In particular, it can be observed that the surface 20 is relatively large compared to the surface of the drop dispenser orifice 16: the surface 20 has an area that is greater than the area of the orifice 16, specifically more than two or three times greater.

Figure 2:
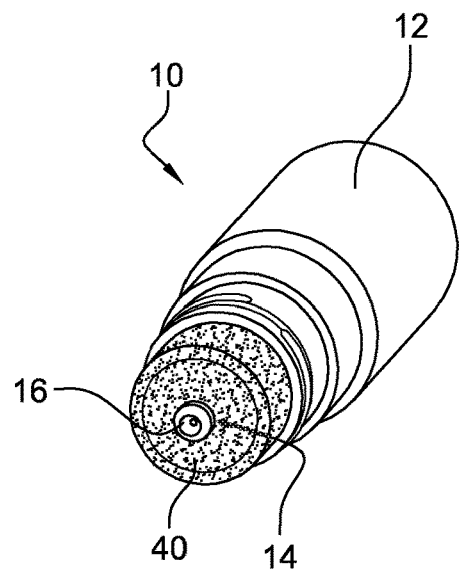
FIG. 2 is a view similar to FIG. 1 in a variant embodiment.

In the embodiment in FIG. 2, the demarcation zone comprises the top surface 20 of the endpiece, as a result of the cap 34 being of a dark color, blue, and the drop-forming means 16 being of a pale color, being white or transparent.

Figure 4:
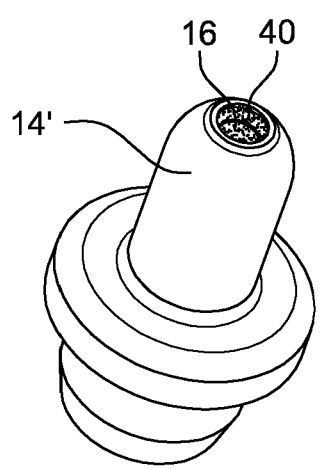
FIG. 4 is a perspective view of a device in a second embodiment.

In the embodiment of FIG. 4, the endpiece 14' is different from the endpiece 14 in that it is in the form of a dispenser nozzle that clearly projects from the remainder of the endpiece. Also, in this embodiment, the top surface of the device is the top of the nozzle and is constituted almost entirely by the drop dispenser orifice. In this embodiment, the demarcation zone 40 is formed by making the drop-forming means 16 dark in color. In this embodiment, the entire drop-forming portion is colored, however, it could be colored in part only.

Figure 5:
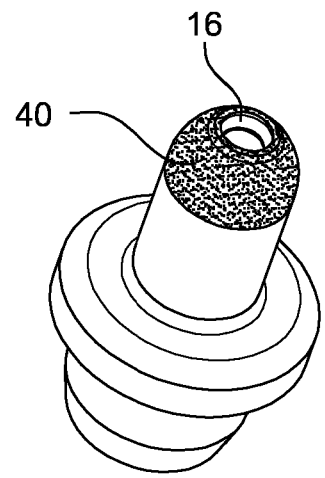
FIGS. 5 to 9 are perspective views of variants of the FIG. 4 device.
Figure 6:
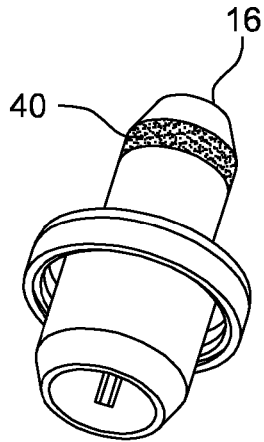
Figure 7:
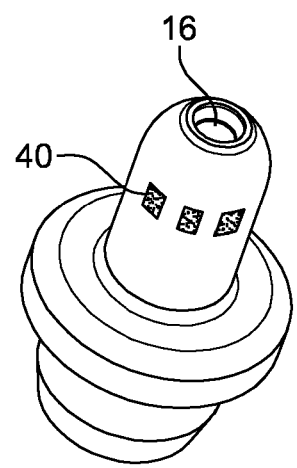
Figure 8:
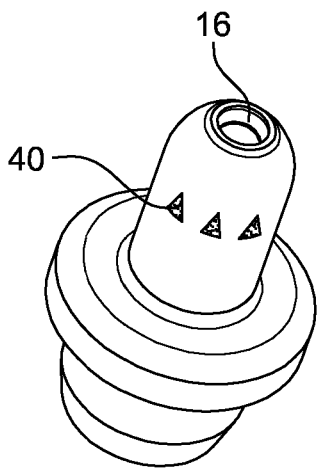
Figure 9:
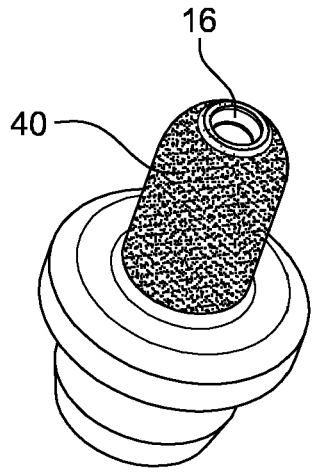

Several variants of demarcation zones 40 on the device in FIG. 4 may be envisaged, in non-limiting manner. In FIG. 5, the demarcation zone 40 is arranged around the dispenser orifice 16 in the form of a dark colored hemisphere, the dispenser orifice 16 being made in a pale color. In FIG. 6, the demarcation zone 40 is also arranged around the dispenser orifice 16 in the form of a dark colored continuous ring, the dispenser orifice 16 being made in a pale color. The colored ring may be formed on an intermediate portion of the nozzle, or indeed in the immediate vicinity of the dispenser orifice, such that the colored ring is arranged on the nozzle just at the periphery of the drop-forming means. In FIG. 7, the demarcation zone 40 is similar to the demarcation zone in FIG. 6 except that the colored ring is discontinuous, by having a circular run of squares or rectangles, which are still dark in color. In FIG. 8, as in FIG. 7, the ring 40 is discontinuous, formed by a circular run of triangles. Finally, in FIG. 9, the demarcation zone 40 is made up of the entire dispenser nozzle, which is made in a dark color, while only the dispenser orifice 16 is made in a pale color.

In the embodiments, it should be observed that the dark-colored demarcation zone may be made by a material that is mass-dyed. Alternatively, it is formed by silk-screen printing, hot marking, printing by ink jet, or by laser marking, so as to apply a preferably dark color on the dispenser end. Thus, in an embodiment, the method of manufacturing the device 10 includes a marking step in order to form the demarcation zone, e.g. a step of silk-screen printing, pad printing, hot marking, printing by ink jet, or laser marking.

The above-described device 10 is very particularly advantageous when it is configured or used for dispensing liquid into an eye.

The invention is not limited to the embodiments described above. In particular, it should be understood that any method can be envisaged for forming a visually contrasting demarcation of the orifice 16 or its vicinity, so as to help the user locate the orifice, very particularly when the user's vision is blurred.

It can also be understood that the characteristics described may be applied to dispenser devices other than those described by way of example, and in particular to a dispenser device without a valve, to a pump, or indeed to a valve.

The invention claimed is:

1. A dispenser device for dispensing liquid in the form of drops, comprising:
   a dispenser end;
   a drop dispenser valve formed of a piece of elastomer material, the drop dispenser valve operable between a liquid-passing configuration and a liquid-blocking configuration;
   a drop dispenser orifice formed in a distal end of the drop dispenser valve including a drop-forming cavity inside the drop dispenser orifice, wherein the drop-forming cavity has a conical shape that flares outwardly and having an inner conical surface;
   a support;
   the dispenser end including a cap for pressing the drop dispenser valve against the support, the cap having an end surface in the shape of a substantially-flat disk with a central hole, the drop dispenser valve extending at least partially through the central hole with the drop dispenser orifice located adjacent to the end surface; and
   an element for visually locating the drop dispenser orifice, the element including a demarcation zone having a color that contrasts with the cap, the demarcation zone obtained by coloring the inner conical surface of the drop-forming cavity inside the drop dispenser orifice.

2. The device according to claim 1, including a dispenser endpiece cylindrical in shape.

3. The device according to claim 1, wherein the disk is of opaque color.

4. The device according to claim 1, wherein the demarcation zone is formed by silk-screen printing, pad printing, hot marking, printing by inkjet, or laser marking.

5. The device according to claim 1, the dispenser device being configured for dispensing liquid in an eye.

6. A method of manufacturing a device according to claim 1, said method including a marking step in order to form the demarcation zone, the marking step including one of a step of silk-screen printing, pad printing, hot marking, printing by inkjet, or laser marking.

7. The device according to claim 1, inside the drop-forming cavity being different in color relative to the other portions of the dispenser end.

8. The device according to claim 1, wherein the cap is white.

9. The device according to claim 1, wherein the drop-forming cavity is different in color relative to the cap.

* * * * *